US009658241B2

(12) United States Patent
Riether et al.

(10) Patent No.: US 9,658,241 B2
(45) Date of Patent: May 23, 2017

(54) SAMPLE DISTRIBUTION SYSTEM AND LABORATORY AUTOMATION SYSTEM

(71) Applicant: Roche Diagnostics Operations, Inc., Indianapolis, IN (US)

(72) Inventors: Christian Riether, Muehltal (DE); Achim Sinz, Waiblingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/665,390

(22) Filed: Mar. 23, 2015

(65) Prior Publication Data

US 2015/0276781 A1 Oct. 1, 2015

(30) Foreign Application Priority Data

Mar. 31, 2014 (EP) .................................... 14162952

(51) Int. Cl.
G06F 7/00 (2006.01)
G01N 35/10 (2006.01)
G01N 27/24 (2006.01)
G01N 35/02 (2006.01)
G01N 35/00 (2006.01)
G01N 35/04 (2006.01)

(52) U.S. Cl.
CPC ......... *G01N 35/1081* (2013.01); *G01N 27/24* (2013.01); *G01N 35/02* (2013.01); *G01N 2035/00277* (2013.01); *G01N 2035/0406* (2013.01); *G01N 2035/0432* (2013.01); *G01N 2035/0437* (2013.01); *G01N 2035/0477* (2013.01)

(58) Field of Classification Search
USPC ........................................................ 700/230
See application file for complete search history.

(56) References Cited

U.S. PATENT DOCUMENTS

| 3,273,727 A | 9/1966 | Rogers et al. |
| 2,653,485 A | 4/1972 | Donlon |
| 3,653,485 A | 4/1972 | Donlon |
| 3,901,656 A | 8/1975 | Durkos et al. |
| 4,150,666 A | 4/1979 | Brush |
| 4,395,164 A | 7/1983 | Beltrop |
| 4,544,068 A | 10/1985 | Cohen |
| 4,771,237 A | 9/1988 | Daley |
| 5,120,506 A | 6/1992 | Saito et al. |
| 5,295,570 A | 3/1994 | Grecksch et al. |
| 5,309,049 A | 5/1994 | Kawada et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |

(Continued)

FOREIGN PATENT DOCUMENTS

| CN | 201045617 Y | 4/2008 |
| CN | 102109530 A | 6/2011 |

(Continued)

*Primary Examiner* — Kyle Logan
(74) *Attorney, Agent, or Firm* — Roche Diagnostics Operations, Inc.

(57) ABSTRACT

A sample distribution system having a transport surface and sample container carriers arranged thereupon is disclosed. A dirt detection device for limiting the effect of dirt is provided.

9 Claims, 1 Drawing Sheet

(56) References Cited

U.S. PATENT DOCUMENTS

| | | |
|---|---|---|
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Thalmayr |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,428,957 B2 | 9/2008 | Schaefer |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,281,888 B2 | 10/2012 | Bergmann |
| 8,796,186 B2 | 8/2014 | Shirazi |
| 9,211,543 B2 | 12/2015 | Ohga et al. |
| 2002/0009391 A1 | 1/2002 | Marquiss et al. |
| 2003/0089581 A1 | 5/2003 | Thompson et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1* | 5/2005 | Thompson ............ B65G 45/24 198/495 |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2008/0012511 A1 | 1/2008 | Ono |
| 2008/0056328 A1 | 3/2008 | Rund et al. |
| 2008/0131961 A1 | 6/2008 | Crees et al. |
| 2008/0286162 A1 | 11/2008 | Onizawa et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | LeComte |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1* | 3/2011 | Furukawa ............ B65G 43/02 324/228 |
| 2011/0172128 A1 | 7/2011 | Davies et al. |
| 2011/0186406 A1* | 8/2011 | Kraus ................ B65G 43/00 198/502.1 |
| 2011/0287447 A1 | 11/2011 | Norderhaug et al. |
| 2012/0037696 A1 | 2/2012 | Lavi |
| 2012/0178170 A1 | 7/2012 | Van Praet |
| 2012/0211645 A1* | 8/2012 | Tullo ................ A61L 2/10 250/214 AL |
| 2012/0275885 A1 | 11/2012 | Furrer et al. |
| 2012/0282683 A1 | 11/2012 | Mototsu |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0231217 A1* | 8/2014 | Denninger ............ B65G 54/02 198/358 |
| 2014/0234065 A1 | 8/2014 | Heise et al. |
| 2014/0234949 A1 | 8/2014 | Wasson et al. |
| 2014/0234978 A1 | 8/2014 | Heise et al. |
| 2015/0014125 A1 | 1/2015 | Hecht |
| 2015/0233956 A1 | 8/2015 | Buehr |
| 2015/0233957 A1 | 8/2015 | Riether |
| 2015/0241457 A1 | 8/2015 | Miller |
| 2015/0273468 A1 | 10/2015 | Croquette et al. |
| 2015/0276775 A1 | 10/2015 | Mellars et al. |
| 2015/0276776 A1 | 10/2015 | Riether |
| 2015/0276777 A1 | 10/2015 | Riether |
| 2015/0276778 A1 | 10/2015 | Riether |
| 2015/0276782 A1 | 10/2015 | Riether |
| 2015/0360876 A1 | 12/2015 | Sinz |
| 2015/0360878 A1 | 12/2015 | Denninger et al. |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0054344 A1 | 2/2016 | Heise et al. |
| 2016/0069715 A1 | 3/2016 | Sinz |
| 2016/0077120 A1 | 3/2016 | Riether |
| 2016/0097786 A1 | 4/2016 | Malinkowski et al. |
| 2016/0229565 A1 | 8/2016 | Margner |
| 2016/0274137 A1 | 9/2016 | Baer |
| 2016/0282378 A1 | 9/2016 | Malinowski et al. |

FOREIGN PATENT DOCUMENTS

| | | |
|---|---|---|
| DE | 3909786 A1 | 9/1990 |
| DE | 102011090044 A1 | 7/2013 |
| EP | 0601213 A1 | 6/1994 |
| EP | 0775650 A1 | 5/1997 |
| EP | 0896936 A1 | 2/1999 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2502675 A1 | 9/2012 |
| EP | 2887071 A1 | 6/2015 |
| GB | 2165515 A | 4/1966 |
| JP | S56-147209 A | 11/1981 |
| JP | 60-223481 A | 11/1985 |
| JP | 61-081323 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 01-148966 A | 6/1989 |
| JP | 01-266860 A | 10/1989 |
| JP | H02-87903 A | 3/1990 |
| JP | 3-112393 A | 5/1991 |
| JP | 03-192013 A | 8/1991 |
| JP | H05-69350 A | 3/1993 |
| JP | H05-180847 A | 7/1993 |
| JP | 06-026808 A | 4/1994 |
| JP | 06-148198 A | 5/1994 |
| JP | 6-156730 A | 6/1994 |
| JP | 06-211306 A | 8/1994 |
| JP | 07-228345 A | 8/1995 |
| JP | 07-236838 A | 9/1995 |
| JP | H11-083865 A | 3/1999 |
| JP | H11-264828 A | 9/1999 |
| JP | H11-304812 A | 11/1999 |

(56) References Cited

FOREIGN PATENT DOCUMENTS

| | | |
|---|---|---|
| JP | H11-326336 A | 11/1999 |
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-062188 A | 3/2009 |
| JP | 2009-145188 A | 7/2009 |
| JP | 2009-300402 A | 12/2009 |
| JP | 2013-172009 A | 9/2013 |
| JP | 2013-190400 A | 9/2013 |
| SU | 685591 A1 | 9/1979 |
| WO | 96/36437 A1 | 11/1996 |
| WO | 03/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2010/085670 A1 | 7/2010 |
| WO | 2012/170636 A1 | 7/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2013/152089 A1 | 10/2013 |
| WO | 2013/169778 A1 | 11/2013 |
| WO | 2014/059134 A1 | 4/2014 |
| WO | 2014/071214 A1 | 5/2014 |

\* cited by examiner

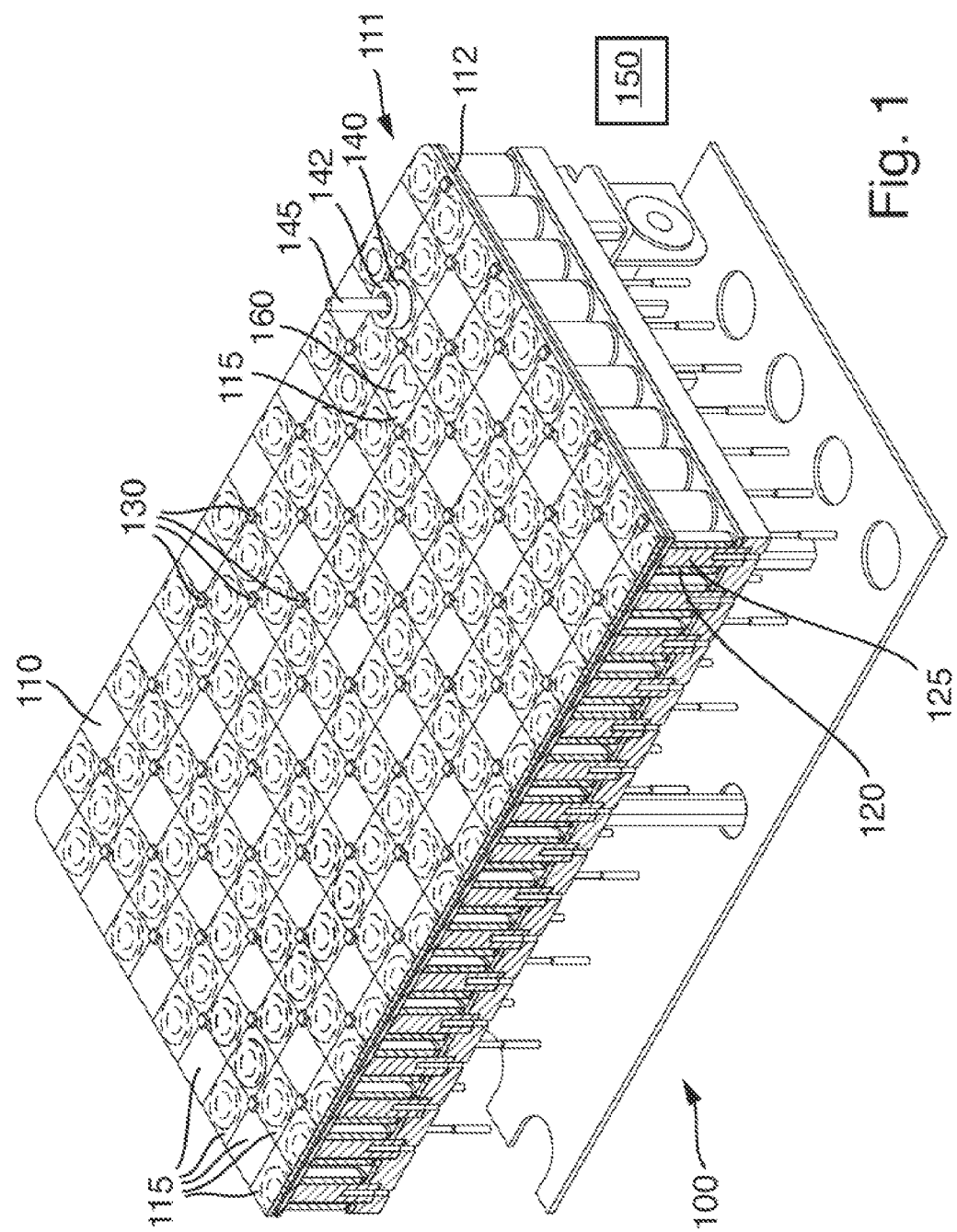

SAMPLE DISTRIBUTION SYSTEM AND LABORATORY AUTOMATION SYSTEM

CROSS-REFERENCE TO RELATED APPLICATIONS

This application claims priority to EP 14162952.7 filed Mar. 31, 2014, which is hereby incorporated by reference.

BACKGROUND

The present disclosure generally relates to a sample distribution system and, in particular, to a sample distribution system comprising a number of sample container carriers, wherein each sample container carrier carries at least one sample container, and to a laboratory automation system comprising such a sample distribution system. The sample distribution system is intended for transporting samples in sample containers to a number of different stations of the laboratory automation system.

It has been found that with generic sample distribution systems there can be situations in which parts of a sample liquid can spill out of a sample container and potentially cause dirt on a transport surface. This can lead to sample container carriers subsequently moving over the polluted place, thereby becoming polluted themselves, and consequently the dirt spreading over the transport surface thus causing cross-contamination.

Therefore, there is a need for a sample distribution system and a laboratory automation system that are improved with respect to the handling of dirt

SUMMARY

According to the present disclosure, a sample distribution system is disclosed. The sample distribution system can comprise a plurality of sample container carriers. Each sample container carrier can carry at least one sample container. A transport surface can carry the plurality of sample container carriers. A plurality of electromagnetic actuators stationary arranged below the transport surface can move a sample container carrier arranged on the transport surface by applying a magnetic force on the sample container carrier. A control device can activate the electromagnetic actuators such that a sample container carrier moves on the transport surface along a predefinable movement path. A dirt detection device detects dirt on the transport surface.

In accordance with one embodiment of the present disclosure, a laboratory automation system is presented. The laboratory automation system can comprise a plurality of pre-analytical, analytical and/or post-analytical stations that process sample containers and/or samples in the sample containers, and a sample distribution system for transporting the sample containers between the pre-analytical, analytical and/or post-analytical stations.

Accordingly, it is a feature of the embodiments of the present disclosure to provide a sample distribution system and a laboratory automation system that are improved with respect to the handling of dirt. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawing, where like structure is indicated with like reference numerals and in which:

FIG. 1 illustrates a sample distribution system according to an embodiment of the present disclosure.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A sample distribution system can comprise a plurality of sample container carriers to carry at least one sample container, a transport surface to carry the plurality of sample container carriers, a driver to move the sample container carriers on the transport surface, and a dirt detection device to detect dirt on the transport surface. Dirt on the transport surface can be detected so that a suitable reaction can follow.

The dirt detection device may detect parameters such as the location, extent, type, area, thickness and/or some other property of the dirt. Depending on this, it is possible for example for appropriate measures to be initiated in an adapted way.

According to an embodiment, in a sample distribution system, a sample container carrier can comprise at least one magnetically active element. The at least one magnetically active element can interact with a magnetic field generated by at least one electromagnetic actuator such that a driving force is applied to the sample container carrier. The driver can comprise a plurality of electromagnetic actuators. The plurality of electromagnetic actuators can be stationary arranged below the transport surface. The electromagnetic actuators can move a sample container carrier arranged on the transport surface by applying a magnetic force on the sample container carrier. The sample distribution system can comprise a control device. The control device can activate the electromagnetic actuators arranged below the transport surface such that a respective sample container carrier can move on the transport surface, in particular two-dimensionally, along a predefinable movement path. In this embodiment, the sample container carriers can be moved by electromagnetic actuators arranged below the transport surface such as, for example, electromagnets.

According to another embodiment, the driver can be a driving device in a sample container carrier. The sample distribution system can comprise a control device. The control device can activate the driving device of the sample container carrier so that the sample container carrier can move on the transport surface along a predefinable movement path. In this embodiment, the sample container carriers can be self-propelling. To receive moving commands, wireless communication may be used. The sample container carriers may, for example, comprise an electric motor and suitable controllers, in order to move independently over the transport surface.

According to another embodiment, the dirt detection device can comprise a plurality of sensor fields. The sensor fields can be distributed on or over the transport surface. Alternatively, the sensor fields may also be distributed under the transport surface. The sensor fields may be distributed uniformly over the (on/under/in the) transport surface. The sensor fields can select at which location on the transport surface dirt is present.

According to another embodiment, a sample container carrier can comprises a dirt sensor. The dirt sensors can be part of the dirt detection device. They may be provided as an alternative, or in addition, to components of the dirt detection device on the transport surface. The arrangement on the sample container carrier can allow a dirt sensor to emit a warning signal and initiate appropriate measures when dirt is only on the sample container carrier but has not yet reached the transport surface. Further instances of contamination can be prevented, for example, by stopping the sample container carrier.

According to another embodiment, the dirt detection device can comprise a capacitive touch-sensitive area. A capacitive touch-sensitive area can be understood to mean an area in which the effective capacitance changes in dependence on being touched or polluted. The capacitive area may be adapted such that a position or location where touching or polluting occurs can be determined. Instances of capacitance-changing polluting can be reliably detected by the capacitive touch-sensitive area. The touch-sensitive area may be arranged in particular on or under the transport surface. It may be divided into individual fields, in order to make possible a positional determination of the dirt.

According to one possible embodiment, the dirt detection device can have a first and a second (capacitor) plate, which can be respectively electrically conductive or electrically conductively coated. This can make possible simple and reliable detection of a change in capacitance on account of dirt. Such a combination of two plates may be provided both on the transport surface and on a sample container carrier.

According to an embodiment, the control device can be in signaling connection with the dirt detection device. The control device can control the movement of the sample container carriers in dependence on detected dirt. This can allow a suitable response to be made to detected dirt. If the dirt detection device is formed in a sample container carrier, a radio link may be provided, for example.

The dirt detection device may determine a position of dirt on the transport surface. The control device can define the movement path of a respective sample container carrier such that it does not run over the position of the dirt. In this way, spreading of the dirt and instances of cross-contamination can be effectively counteracted.

The dirt detection device may also determine parameters such as the location, extent, type, area, thickness and/or other properties of dirt. The control device can also be able to use such properties in a response to the dirt for controlling the movement of the sample container carriers on the transport surface.

For example, an exclusion area, for example, a circle with a specific radius or a square with a specific edge length, may be established around the position of the dirt. No sample container carrier can move into this exclusion area until the dirt has been removed.

According to an embodiment, the control device may stop possible movement of sample container carriers, which may be located at the position of the dirt, or at a predefined distance from it, after detection of the dirt. In this way, it can prevent a sample container carrier located directly alongside the dirt, and with a high degree of probability will consequently be contaminated with the dirt, from continuing to move on the transport surface, and thereby spreading the dirt on the transport surface. For example, all sample container carriers within the exclusion area may be stopped. This exclusion area may also be used separately for the purpose of stopping sample container carriers.

According to an embodiment, the control device can stop or halt all the sample container carriers when dirt is detected. In this way, particularly reliable prevention of the spreading of the dirt can be achieved. Furthermore, this embodiment can be applied in particular whenever the dirt detection device is not adapted for detecting the position of dirt on the transport surface.

The laboratory automation system can comprises a plurality (for example, between two and twenty) of pre-analytical and/or analytical and/or post-analytical stations, which can work on or can process sample containers and/or samples contained in the sample containers. The working or processing may, for example, comprise reading a barcode, removing a cap on the tube, centrifuging the sample, aliquoting the sample, analyzing the sample, and the like. The laboratory automation system can also comprise a sample distribution system for transporting the sample containers between the pre-analytical, analytical and post-analytical stations.

The pre-analytical, analytical and post-analytical stations may, for example, comprise at least one station from the list of following stations: a cap-removing station for removing caps or closures on sample tubes, a cap-positioning station for placing caps or closures in position on sample tubes, an aliquoting station for aliquoting samples, a centrifugal station for centrifuging samples, an archiving station for archiving samples, a pipetting station for pipetting, a sorting station for sorting samples or sample tubes, a sample-tube-type determining station for determining a type of sample tube and a sample-quality determining station for determining a sample quality.

FIG. 1 shows a sample distribution system 100. The sample distribution system 100 can comprise a transport surface 110, on which a plurality of sample container carriers 140 can be placed. Here, only one sample container carrier 140 is shown by way of example, with a sample container 145 contained therein in the form of a sample tube.

Formed on the transport surface 110 can be a dirt detection device 111 having a capacitive touch-sensitive area 112, which can be formed by two plates. Each of the two plates can have an electrically conductive coating. In this way, a change in capacitance that can be caused by dirt 160 on the dirt detection device 111 can be detected by suitable measuring devices.

The area 112 can be divided into a multiplicity of fields 115. Each field 115 can be measured with regard to its capacitance individually and independently of the other fields 115. This can make it possible not only to detect dirt 160 on the transport surface 110, but also to ascertain its precise location.

Arranged under the area 112 can be a plurality of electromagnetic actuators in the form of electromagnets 120 with respective cores 125. In the sample container carrier 140, there can be a permanent magnet, so that a force can be exerted on the sample container carrier 140 by suitable activation of the electromagnets 120. In this way, the sample container carrier 140 can be moved over the transport surface 110.

In order to detect a position of a sample container carrier 140 on the transport surface 110, a plurality of Hall sensors 130 can be arranged on the transport surface 110.

As shown, each of the fields 115 can either be assigned an electromagnet 120 or not assigned an electromagnet. The fields 115 can, in each case, be substantially square and can be distributed uniformly over the transport surface 110 alongside one another.

Dirt 160 on the transport surface 110 is shown by way of example. The dirt detection device 111 can detect by the capacitive touch-sensitive area 112 on the corresponding field 115 on which the dirt 160 may be located a change in the capacitance between the two plates. In this way, the dirt 160 can be detected and its position can be located.

For monitoring the dirt detection device 111 and for controlling respective power supplies to the magnets 120, a control device 150 can be provided. The control device 150 can detect and ascertain the precise location of dirt 160 on the basis of the signals sent from the dirt detection device 111, i.e. from the area 112 or the fields 115 thereof. As shown, the sample container carrier 140 can be located directly alongside the dirt 160. Here, the control device 150 can be adapted such that, in such a case, it can stop the movement of the sample container carrier 140. In this way, spreading of the dirt 160 over the transport surface 110 by the sample container carrier 140 can be prevented.

The sample container carrier 140 furthermore can have a surface 142, which can be formed as a dirt detection sensor or dirt sensor. The dirt detection sensors of all the sample container carriers can be parts of the dirt detection device 111.

The surface or the dirt detection sensor 142 may be formed as a capacitive sensor having two plates with a electrically conductive coating. Spilling at least partially of the liquid sample contained in the sample tube 145 can be detected by the dirt detection sensor before ingredients of the sample pollute the transport surface 110.

The sample container carrier 140 may have a wireless data transmission device for transmitting information concerning detected dirt to the control device 150. In this event, the movement of the sample container carrier 140 may be stopped or halted immediately, in order to avoid further spreading of the dirt.

The control device 150 can further move sample container carriers 140, which are moving on the transport surface 110, around detected dirt 160. For this purpose, predefinable movement paths can be suitably recalculated.

The sample distribution system 100 can be part of a laboratory automation system comprising a number of pre-analytical, analytical and post-analytical stations that are arranged alongside the transport surface 110. The sample distribution system 100 can serve for transporting the sample containers between these stations.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A sample distribution system, the sample distribution system comprising:
   a plurality of sample container carriers, wherein each sample container carrier carries at least one sample container;
   a transport surface, wherein the transport surface carries the plurality of sample container carriers;
   a plurality of electromagnetic actuators, wherein the plurality of electromagnetic actuators is stationary arranged below the transport surface, wherein the electromagnetic actuators move a sample container carrier arranged on the transport surface by applying a magnetic force on the sample container carrier;
   a control device, wherein the control device activates the electromagnetic actuators such that a sample container carrier moves on the transport surface along a predefinable movement path; and
   a dirt detection device, wherein the dirt detection device detects dirt on the transport surface and determines a position of dirt on the transport surface,
   wherein the control device is in signaling connection with the dirt detection device and wherein the control device defines the movement path of a sample container carrier such that it does not run over the position of dirt.

2. The sample distribution system according to claim 1, wherein the dirt detection device comprises a plurality of sensor fields distributed over the transport surface.

3. The sample distribution system according to claim 1, wherein the dirt detection device comprises a capacitive touch-sensitive area.

4. The sample distribution system according to claim 1, wherein the control device controls the movement of the sample container carriers in dependence on detected dirt.

5. The sample distribution system according to claim 1, wherein the control device stops all the sample container carriers after detection of dirt.

6. A sample distribution system, the sample distribution system comprising:
   a plurality of sample container carriers, wherein each sample container carrier carries at least one sample container, wherein each sample container carrier comprises a dirt sensor, and wherein the dirt sensors are a part of the dirt detection device;
   a transport surface, wherein the transport surface carries the plurality of sample container carriers;
   a plurality of electromagnetic actuators, wherein the plurality of electromagnetic actuators is stationary arranged below the transport surface, wherein the electromagnetic actuators move a sample container carrier arranged on the transport surface by applying a magnetic force on the sample container carrier;
   a control device, wherein the control device activates the electromagnetic actuators such that a sample container carrier moves on the transport surface along a predefinable movement path; and
   a dirt detection device, wherein the dirt detection device detects dirt on the transport surface and determines a position of dirt on the transport surface, wherein the control device is in signaling connection with the dirt detection device.

7. A sample distribution system, the sample distribution system comprising:
- a plurality of sample container carriers, wherein each sample container carrier carries at least one sample container;
- a transport surface, wherein the transport surface carries the plurality of sample container carriers;
- a plurality of electromagnetic actuators, wherein the plurality of electromagnetic actuators is stationary arranged below the transport surface, wherein the electromagnetic actuators move a sample container carrier arranged on the transport surface by applying a magnetic force on the sample container carrier;
- a control device, wherein the control device activates the electromagnetic actuators such that a sample container carrier moves on the transport surface along a predefinable movement path; and
- a dirt detection device, wherein the dirt detection device detects dirt on the transport surface and determines a position of dirt on the transport surface,
- wherein the control device is in signaling connection with the dirt detection device and wherein the control device stops sample container carriers located at the position of dirt, or at a predefinable distance from it, after detection of dirt.

8. A laboratory automation system, the laboratory automation system comprising:
- a plurality of pre-analytical, analytical and/or post-analytical stations that process sample containers and/or samples in the sample containers; and
- a sample distribution system for transporting the sample containers between the pre-analytical, analytical and/or post-analytical stations according to claim 1.

9. A sample distribution system, the sample distribution system comprising:
- a plurality of sample container carriers, wherein each sample container carrier carries at least one sample container;
- a transport surface, wherein the transport surface carries the plurality of sample container carriers;
- a plurality of electromagnetic actuators, wherein the plurality of electromagnetic actuators is stationary arranged below the transport surface, wherein the electromagnetic actuators move a sample container carrier arranged on the transport surface by applying a magnetic force on the sample container carrier;
- a control device, wherein the control device activates the electromagnetic actuators such that a sample container carrier moves on the transport surface along a predefinable movement path; and
- a dirt detection device, wherein the dirt detection device comprises a plurality of sensor fields distributed over the transport surface and wherein the dirt detection device detects dirt on the transport surface,
- wherein the control device defines the movement path of a sample container carrier such that it does not run over the dirt.

* * * * *